United States Patent [19]

Shawver

[11] Plant 4,442

[45] Jul. 24, 1979

[54] FUCHSIA PLANT

[76] Inventor: James R. Shawver, 281 S. Job St., Virginia, Ill. 62691

[21] Appl. No.: 921,461

[22] Filed: Jul. 5, 1978

[51] Int. Cl.[2] ..... A01H 5/00
[52] U.S. Cl. ..... Plt./84
[58] Field of Search ..... Plt./84

*Primary Examiner*—Robert E. Bagwill
*Attorney, Agent, or Firm*—John Shaw Stevenson

[57] ABSTRACT

This invention relates to a new and improved fuchsia plant, the principal new and different characteristic of which is the combination of the rose red sepals with the lavender corolla.

2 Drawing Figures

1

The plant was derived as a sport from the fuchsia, Dark Eyes, each flower of which has a large, violet-blue corolla and red sepals. The fuchsia plant is distinguished principally by its deep to medium green foliage, vigorous trailing habit of growth, distinctive rose red sepals and lavender colored corolla marked with rose red veins, which have not previously been found in this combination in any other trailing fuchsia plant, and has been asexually reproduced in Springfield, Ill., from a cultivated sport cutting taken from the parent plant. Because of its unique color combination, it is unusually decorative in hanging baskets.

The plant is of a trailing variety and grows vigorously, throwing many trailing branches during the process of growth. When the plant blooms, the round, slightly flat, rose red colored buds open into large double flowers and expose a corolla that is of a lavender color (RHS 76A). The flower has no fragrance.

In the accompanying illustrations, the lower figure shows the branch tips, including both buds and fully opened blossoms, the illustration representing the actual size.

A detailed description of the new variety of plant follows:

Habit of growth: Strong, trailing variety that grows vigorously, throwing out numerous trailing branches, which in turn are self-branching. Flowers occur both along the stem and at the tips of the branches.

Foliage: Medium sized, medium to dark green leaves, deeply veined, having smooth edges, evenly spaced along the branches. The leaves are of a general broad heart shape, the buds are short, round and slightly flat

2 on the bottom and are rose red in color. (Exotica Color Chart 31+).

Flower: The flower is double, of medium size. The corolla is open and flaring. The color is lavender (RHS 76A) which is the outstanding difference and distinctive feature of this plant.

Ovary: Medium small and light green.

Style: Short, broad and rose red. (Exotica Color Chart 31+).

Petals: The centrally located petals are substantially of a small, tulip shaped configuration while the outer petals are clustered in a flared array. Both the centrally located and outer petals are of a lavender color (RHS 76A) and have rose red (Exotica Color Chart 31+) vein markings as above described.

Stamens: The stamens are long, approximately 2–2½ inches in length measured from the peduncle to the stigma and are of a rose red color (Exotica Color Chart 31+).

Sepals: Rose red (Exotica Color Chart 31+).

Parentage: This fuchsia was derived as a sport from Dark Eyes.

It is noted that the foliage and flowers will vary somewhat with the seasons and growing conditions; however, the fuchsia plant is clearly differentiated from others by the lavender color of the petals.

Having thus disclosed by discovery I claim:

1. The new and distinct variety of fuchsia plant herein described and illustrated, characterized by the rose red sepals in combination with the lavender petals marked with rose red veins.

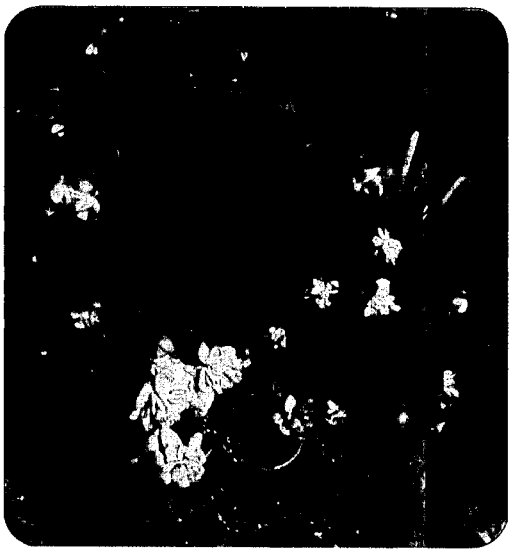
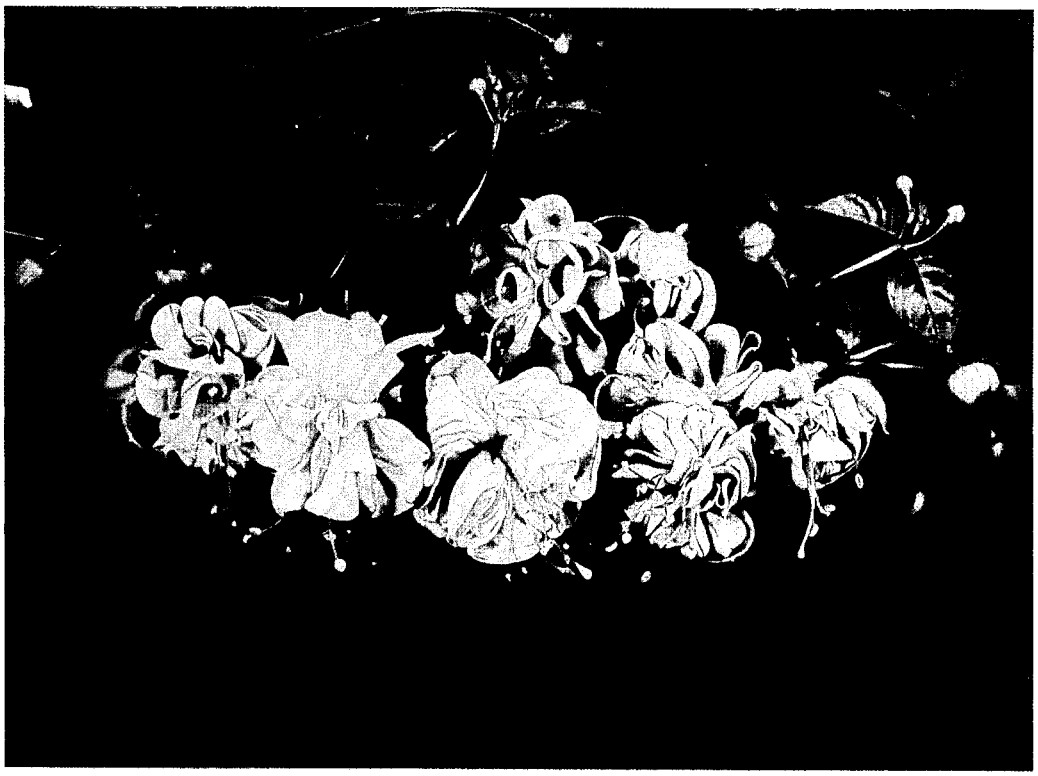

* * * * *